US012569656B2

(12) United States Patent 
Guo et al.

(10) Patent No.: US 12,569,656 B2 
(45) Date of Patent: Mar. 10, 2026

(54) URETERAL STENT AND MANUFACTURING METHOD THEREOF

(71) Applicant: HONEST MEDICAL CHINA CO., LTD., Zhuhai (CN)

(72) Inventors: Aijun Guo, Zhuhai (CN); Zhirong Li, Zhuhai (CN); Jianjin Wang, Zhuhai (CN)

(73) Assignee: HONEST MEDICAL CHINA CO., LTD., Zhuhai (CN)

( * ) Notice: Subject to any disclaimer, the term of this patent is extended or adjusted under 35 U.S.C. 154(b) by 336 days.

(21) Appl. No.: 18/278,843

(22) PCT Filed: Mar. 25, 2022

(86) PCT No.: PCT/CN2022/082939 
§ 371 (c)(1), 
(2) Date: Aug. 25, 2023

(87) PCT Pub. No.: WO2022/222684 
PCT Pub. Date: Oct. 27, 2022

(65) Prior Publication Data 
US 2024/0131308 A1 Apr. 25, 2024 
US 2024/0226513 A9 Jul. 11, 2024

(30) Foreign Application Priority Data

Apr. 19, 2021 (CN) .......................... 202110418367.5

(51) Int. Cl. 
*A61M 27/00* (2006.01)

(52) U.S. Cl. 
CPC ....... *A61M 27/008* (2013.01); *A61M 2207/10* (2013.01); *A61M 2210/1089* (2013.01)

(58) Field of Classification Search 
CPC ........ A61M 27/008; A61M 2210/1078; A61M 2210/1089; A61M 25/0045; 
(Continued)

(56) References Cited

U.S. PATENT DOCUMENTS 5,876,445 A * 3/1999 Andersen ................ A61L 31/04 
623/23.7 
6,245,100 B1 6/2001 Davila et al. 
(Continued)

FOREIGN PATENT DOCUMENTS

CN 101496754 A 8/2009 
CN 102438558 A 5/2012 
(Continued)

OTHER PUBLICATIONS

International Search Report of PCT Patent Application No. PCT/CN2022/082939 issued on May 27, 2022.

*Primary Examiner* — Adam Marcetich

(57) ABSTRACT

A ureteral stent and a manufacturing method of a ureteral stent are applied to the technical field of medical instruments, to effectively reduce ureteral stent failure in fluid guiding. The ureteral stent comprises an inner structure (200), and an outer structure (100) sleeved on the inner structure (200), wherein the outer structure (100) is a tube-shaped structure, and the outer structure (100) is made from a first wire (110). The ureteral stent can effectively reduce ureteral stent failure in fluid guiding.

9 Claims, 7 Drawing Sheets

(58) Field of Classification Search
CPC ........ A61M 27/002; A61M 2025/0024; A61M
2205/0266; A61F 2002/048; A61F 2/04;
A61F 2/94; A61F 2/88; A61F 2210/0076;
A61F 2/852; A61F 2/90; A61F 2/07;
A61F 2/82; A61F 2210/0014; A61F
2230/0091; A61F 2230/0069
See application file for complete search history.

(56) References Cited

U.S. PATENT DOCUMENTS

| | | | | |
|---|---|---|---|---|
| 6,395,021 | B1 * | 5/2002 | Hart | A61F 2/82 |
| | | | | 623/1.2 |
| 6,582,472 | B2 * | 6/2003 | Hart | A61F 2/95 |
| | | | | 623/1.2 |
| 2003/0040754 | A1 * | 2/2003 | Mitchell | A61B 17/221 |
| | | | | 606/106 |
| 2003/0216804 | A1 * | 11/2003 | DeBeer | A61F 2/91 |
| | | | | 623/1.49 |
| 2004/0138644 | A1 * | 7/2004 | DiCarlo | A61M 25/0043 |
| | | | | 604/524 |
| 2005/0070995 | A1 * | 3/2005 | Zilla | A61L 27/14 |
| | | | | 600/36 |
| 2005/0192662 | A1 | 9/2005 | Ward | |
| 2005/0240278 | A1 * | 10/2005 | Aliski | A61F 2/04 |
| | | | | 604/8 |
| 2009/0192588 | A1 * | 7/2009 | Shin | A61F 2/04 |
| | | | | 623/1.38 |
| 2010/0145467 | A1 * | 6/2010 | Davoudi | A61M 25/0043 |
| | | | | 623/23.7 |
| 2014/0005713 | A1 * | 1/2014 | Bowman | A61B 17/22032 |
| | | | | 606/200 |
| 2015/0148882 | A1 * | 5/2015 | Ma | A61F 2/06 |
| | | | | 623/1.2 |
| 2016/0310299 | A1 * | 10/2016 | Mangiardi | A61F 2/844 |
| 2017/0156842 | A1 | 6/2017 | Isch et al. | |
| 2018/0318115 | A1 | 11/2018 | Chinubhai et al. | |
| 2019/0167455 | A1 | 6/2019 | Myung | |
| 2020/0046527 | A1 * | 2/2020 | Kónya | A61F 2/07 |
| 2020/0229955 | A1 * | 7/2020 | Uesugi | A61F 2/95 |
| 2022/0265449 | A1 * | 8/2022 | Bonera | A61F 2/04 |

FOREIGN PATENT DOCUMENTS

| | | | | |
|---|---|---|---|---|
| CN | 102858280 A | | 1/2013 | |
| CN | 104042376 A | | 9/2014 | |
| CN | 104487024 A | | 4/2015 | |
| CN | 106691646 A | | 5/2017 | |
| CN | 109414332 A | | 3/2019 | |
| CN | 113613600 A | | 11/2021 | |
| GB | 2464765 A | * | 5/2010 | A61N 5/1001 |
| WO | WO-2008034341 A1 | * | 3/2008 | A61M 27/008 |
| WO | 2020/196912 A1 | | 10/2020 | |

* cited by examiner

URETERAL STENT AND MANUFACTURING METHOD THEREOF

TECHNICAL FIELD

The disclosure relates to the technical field of medical instruments, and more particularly to a ureteral stent and a manufacturing method thereof.

BACKGROUND

Invasive surgeries are applied to the treatment of ureteral obstruction, hydronephrosis and the like for diseases such as tumors, retroperitoneal fibrosis, and ureterostenosis. During surgeries, the ureteral stent for supporting the ureter may be placed within the ureter, to avoid ureterostenosis, ureter adhesions and ureteral obstruction, and enable the urine to flow from the renal pelvis to the bladder.

Conventional ureteral stents, which are widely used in hospitals and are referred to as pigtail stents, are usually made from polyurethane. They have high radial strength and are not readily deformable. Furthermore, a pigtail stent usually has a side wall provided with a number of through holes to facilitate better fluid guiding performance. However, the through holes may be blocked by proliferative tissues after prolonged periods of use, which may lead to stent failure in fluid guiding.

SUMMARY

The disclosure is to overcome at least an existing technical problem of the prior art. To this end, the disclosure provides a ureteral stent for effectively reducing ureteral stent failure in fluid guiding.

A ureteral stent according to a first aspect of the disclosure comprises: an inner structure, and an outer structure sleeved on the inner structure, wherein the outer structure is a tube-shaped structure, and the outer structure is made from a first wire.

In some embodiments of the disclosure, the first wire may be an elastic thread.

In some embodiments of the disclosure, the first wire may be a memory alloy thread.

In some embodiments of the disclosure, the first wire may be bent to form loops passing through one another to constitute the outer structure.

In some embodiments of the disclosure, segments of the first wire interlacing in a first direction and a second direction may constitute the outer structure, wherein the first direction and the second direction may be perpendicular to each other.

In some embodiments of the disclosure, the inner structure may be at least made of a strand of second wire, and the knitted second wire may be provided with fluid guiding gaps for fluid guiding therein.

In some embodiments of the disclosure, both ends of the ureteral stent may be bent, and the two ends of the ureteral stent may be bent in opposite directions.

A manufacturing method of a ureteral stent according to a second aspect of the disclosure, for manufacturing the above ureteral stent, comprises steps as follows: preparing the outer structure with the first wire, and then sleeving the outer structure on the inner structure.

In some embodiments of the disclosure, using knitting method, in which the first wire is bent to form loops passing through one another to constitute the outer structure.

In some embodiments of the disclosure, using woven method, in which segments of the first wire interlace with one another in a first direction and a second direction to constitute the outer structure, wherein the first direction and the second direction are perpendicular to each other.

The ureteral stent of the disclosure can be applied as follows. During use, the tube-shaped outer layer may be radially compressed and then placed in the urethra by an implant device, to provide a support in the urethra. When the outer structure deforms, the outer structure supported by the inner structure would not deform too much to completely fold up due to the inner structure that provides a support inside the outer structure. In such a case, the urine can flow along the gaps formed by the first wire of the outer layer. Thus, the outer structure still has an effect on urinary catheterization. Consequently, the ureteral stent failure in fluid guiding can be effectively reduced.

Some additional aspects and advantages of the disclosure will be set forth in the description below, and some will be apparent from the description, or may be learned by practice of the invention.

BRIEF DESCRIPTION OF THE DRAWINGS

The above and/or other aspects and advantages of the present invention will be more apparent and easy to understand from the following description of drawings for the embodiments. Herein.

Figure 1:
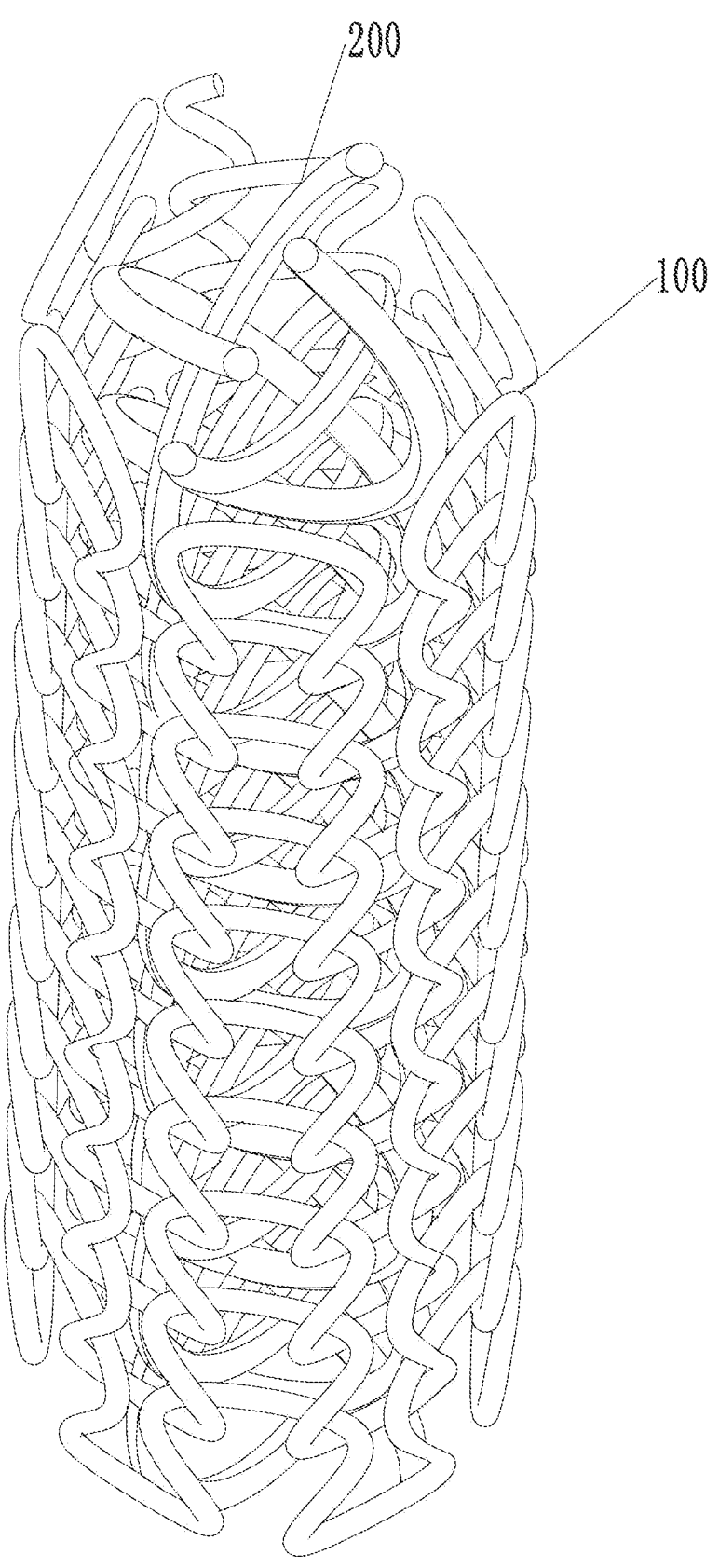
FIG. 1 is an assembly isometric view illustrating an inner structure and an outer structure of a ureteral stent assembly according to an embodiment of the disclosure.

The above drawings use reference signs as follows.

| Reference signs | Parts |
| --- | --- |
| 100 | outer structure |
| 110 | first wire |
| 200 | inner structure |
| 210 | second wire |

DETAILED DESCRIPTION OF ILLUSTRATED EMBODIMENTS

The embodiments of the disclosure will be described in detail below. Examples of the embodiments are illustrated in the drawings. It should be understood that identical or same reference signs throughout the text indicate the identical or same elements or the elements with identical or same functions. The embodiments described below in conjunction with the drawings are exemplary and are intended for purposes of illustration only, and are not intended to limit the scope.

It should be understood that, for convenience of description and simplify the explanation, the terms such as "up", "down", "front", "rear", "left" and "right" used in the description refer to position and orientation relationships depicted in the drawings. It is not intended to limit the disclosure by indicating or hinting devices or components having particular orientation relationships or being construed or operated with particular orientation relationships.

In the description of the disclosure, the term "several" means one or plurality, the term "plurality" means two or more than two, terms such as "greater than", "less than" and "exceed" should be understood to exclude the boundary value, and terms such as "above", "below" and "within" should be understood to include the boundary value. In addition, terms such as "first" and "second" used herein are merely intended to distinct the features from each other, but are not intended to indicate or hint relative importance or quantity or precedence relationship of the characteristics.

Unless defined otherwise, terms such as "arrange", "mount" and "connect" used herein are intended to have the meanings commonly understood in a broad sense based on particular content of the technical solution by those skilled in the art.

Figure 2:
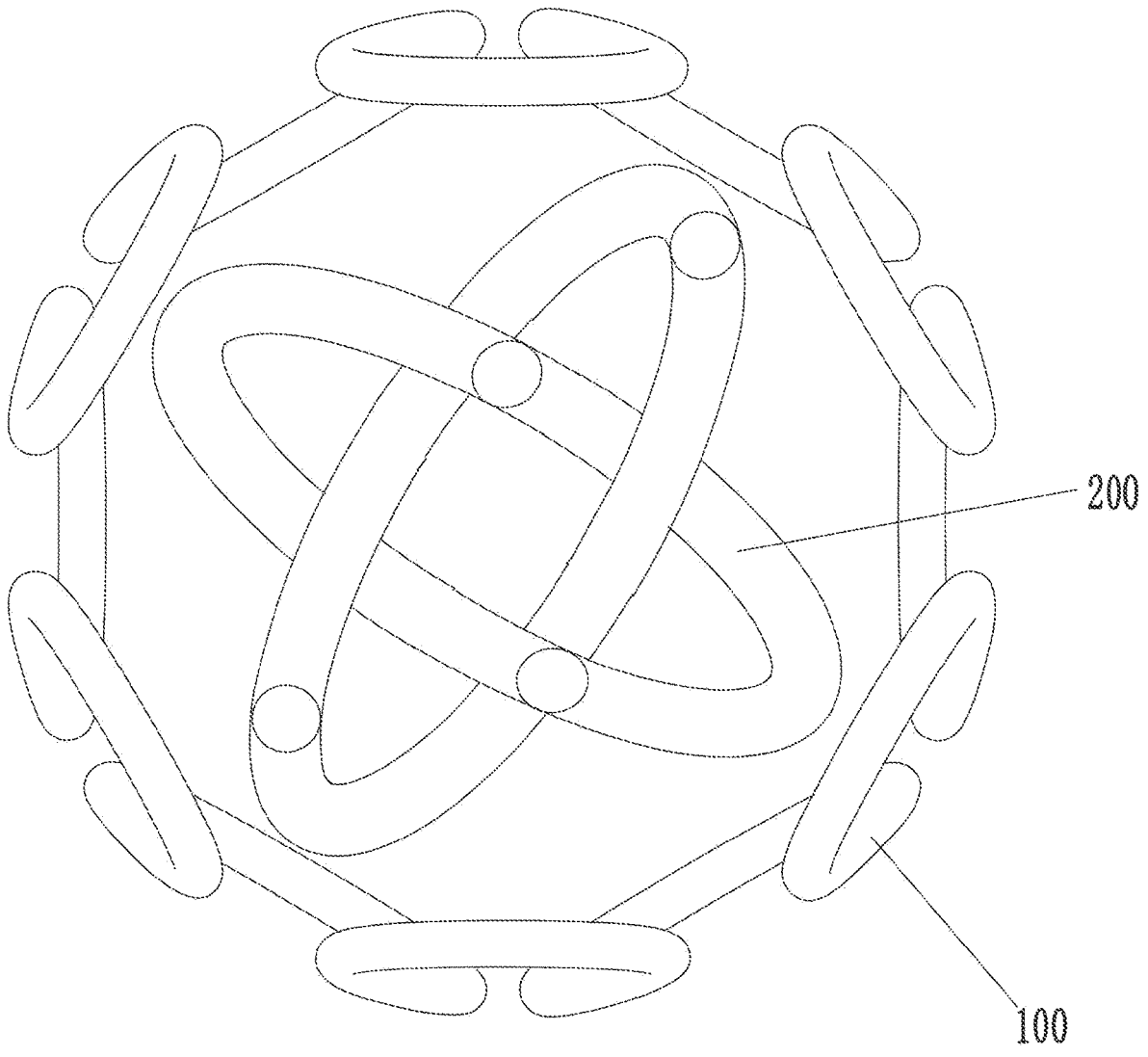
FIG. 2 is an assembly top view illustrating an inner structure and an outer structure of a ureteral stent assembly according to an embodiment of the disclosure.

Referring to FIGS. 1 and 2, a ureteral stent according to an embodiment of the first aspect of the disclosure comprises an inner structure 200, and an outer structure 100 sleeved on the inner structure 200. Herein, the outer structure 100 is a tube-shaped structure, and the outer structure 100 is knitted with the first wire 110.

The ureteral stent according to the present embodiment of the first aspect of the disclosure can be applied as follows. During use, the tube-shaped outer layer may be radially compressed and then placed in the urethra by an implant device, to provide a support in the urethra. When the outer structure 100 deforms, the outer structure 100 supported by the inner structure 200 would not deform too much to completely fold up due to the inner structure 200 that provides a support inside the outer structure 100. In such a case, the urine can flow along the gaps formed by the first wire 110 of the outer layer. Thus, the outer structure 100 still has an effect on urinary catheterization. Consequently, the ureteral stent failure in fluid guiding can be effectively reduced.

In another aspect, in the case that the outer structure 100 is a structure formed by tightly knitting the first wire 110, fluid guiding gaps for fluid guiding can be formed by the first wire 110. In addition, the tightly knitted structure can prevent proliferative tissues from accessing to the passage and blocking the urine guiding passage.

Herein, in order to improve deformation performance of the ureteral stent to enable the outer structure 100 to provide a support for the urethra even when the outer structure 100 is compressed, it is conceivable to use the first wire 110 which is made of elastic thread. Herein, the elastic thread may be made from hyperelastic materials of shape memory alloy, for example, Nitinol alloy. Alternatively, it is also conceivable to use high polymer materials having high elasticity.

Figure 3:
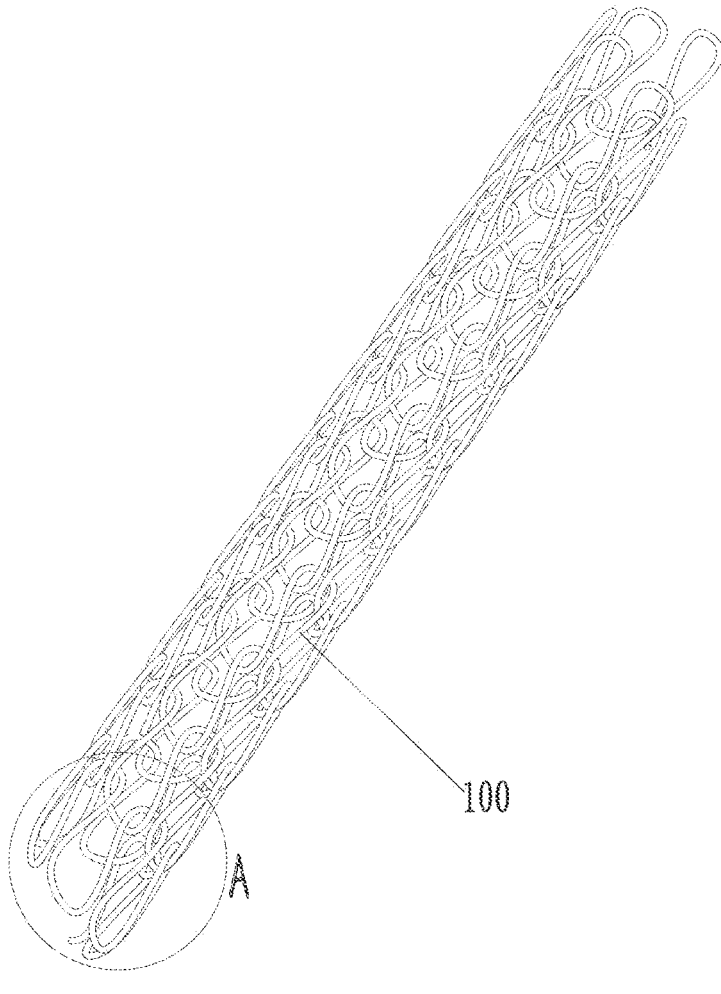
FIG. 3 is an isometric view of an outer structure according to an embodiment of the disclosure.
Figure 4:
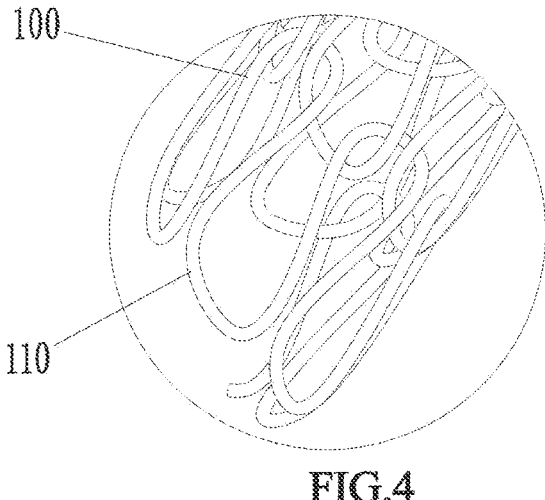
FIG. 4 is an enlarged view illustrating the area A of FIG. 3.

Referring to FIGS. 3 and 4, the outer structure 100 may be produced by knitting method. In such a case, the first wire 110 may be bent to form loops passing through one another to constitute the outer structure 100.

Figure 5:
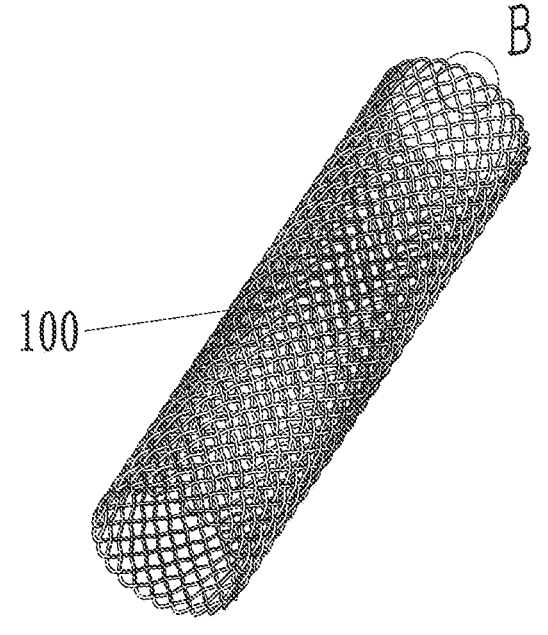
FIG. 5 is an isometric view of another outer structure according to an embodiment of the disclosure.
Figure 6:
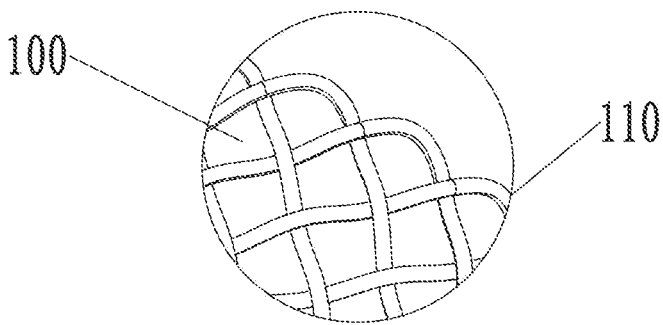
FIG. 6 is an enlarged view illustrating the area B of FIG. 5.

Referring to FIGS. 5 and 6, the outer structure 100 may be produced by woven method. In such a case, segments of the first wire 110 interlace with one another in a first direction and a second direction to constitute the outer structure 100. Herein, the first direction and the second direction are perpendicular to each other.

Referring to FIGS. 7-11, the inner structure 200 is at least made of a strand of second wire 210, and the second wire 210 that is made is provided with fluid guiding gaps for fluid guiding. Herein, the urine can flow through the fluid guiding gaps formed by the second wire 210 of the outer layer and gradually flow from the renal pelvis to the bladder. In such a case, the outer structure 100 can have a good effect on urine guiding even when being compressed.

In the embodiment, both ends of the ureteral stent are bent, and the two ends of the ureteral stent are bent in opposite directions. In such a case, the ureteral stent may have a profile similar to the pigtail stents widely used in the prior arts for urinary catheterization, which effectively avoids displacement of the ureteral stent in the ureter.

A first aspect of the embodiment further provides a manufacturing method of the ureteral stent for manufacturing the above-mentioned ureteral stent. The method comprises steps as follows: preparing the outer structure 100 with the first wire 110, and then sleeving the outer structure 100 on the inner structure 200.

Herein, the outer structure 100 may be produced by knitting method, in which the first wire 110 is bent to form loops passing through one another to constitute the outer structure 100. Alternatively, it may be produced by woven method, in which segments of the first wire 110 interlacing in the first direction and the second direction constitute the outer structure 100. Herein, the first direction and the second direction are perpendicular to each other. In the woven method, the first wire 110 extending in the first direction during preparing is the warp strand, and the second wire 210 extending in the second direction during preparing is the weft strand.

The second aspect of the embodiment further provides a ureteral stent, which comprises an inner structure 200, and an outer structure 100 sleeved on the inner structure 200. Herein, the inner structure 200 is provided with fluid guiding gaps which allow the urine to flow therethrough.

The ureteral stent according to the present embodiment of the second aspect of the disclosure can be applied as follows. During use, the tube-shaped outer layer may be compressed and then placed in the urethra by an implant device, to provide a urine guiding passage in the urethra. In such a case, the urine can flow along the fluid guiding gaps formed by the inner structure 200 even when the outer structure 100 is maximally compressed to tightly abut against the inner layer. Thus, the ureteral stent failure in fluid guiding is effectively reduced.

Referring to FIGS. 7-11, the inner structure 200 is a rope-shaped structure made from the second wire 210, and the second wire 210 that is woven is provided with fluid guiding gaps. As the inner structure 200 is a rope-shaped structure which cannot be radially compressed, it has a good effect on fluid guiding when the outer structure 100 is compressed. In addition, the second wire 210 that is woven provides fluid guiding gaps for urine guiding, such that the ureteral stent can have a good effect on fluid guiding even when being compressed.

Similar to the first wire 110, the second wire 210 may be made of elastic thread. Herein, the elastic thread may be made from hyperelastic materials of shape memory alloy, for example, nickel titanium alloy. Alternatively, it is also conceivable to use high polymer materials having high elasticity.

Referring to FIGS. 8-11, the second wire 210 may be woven to the inner structure 200 in various manners. Details are discussed below.

Figure 7:
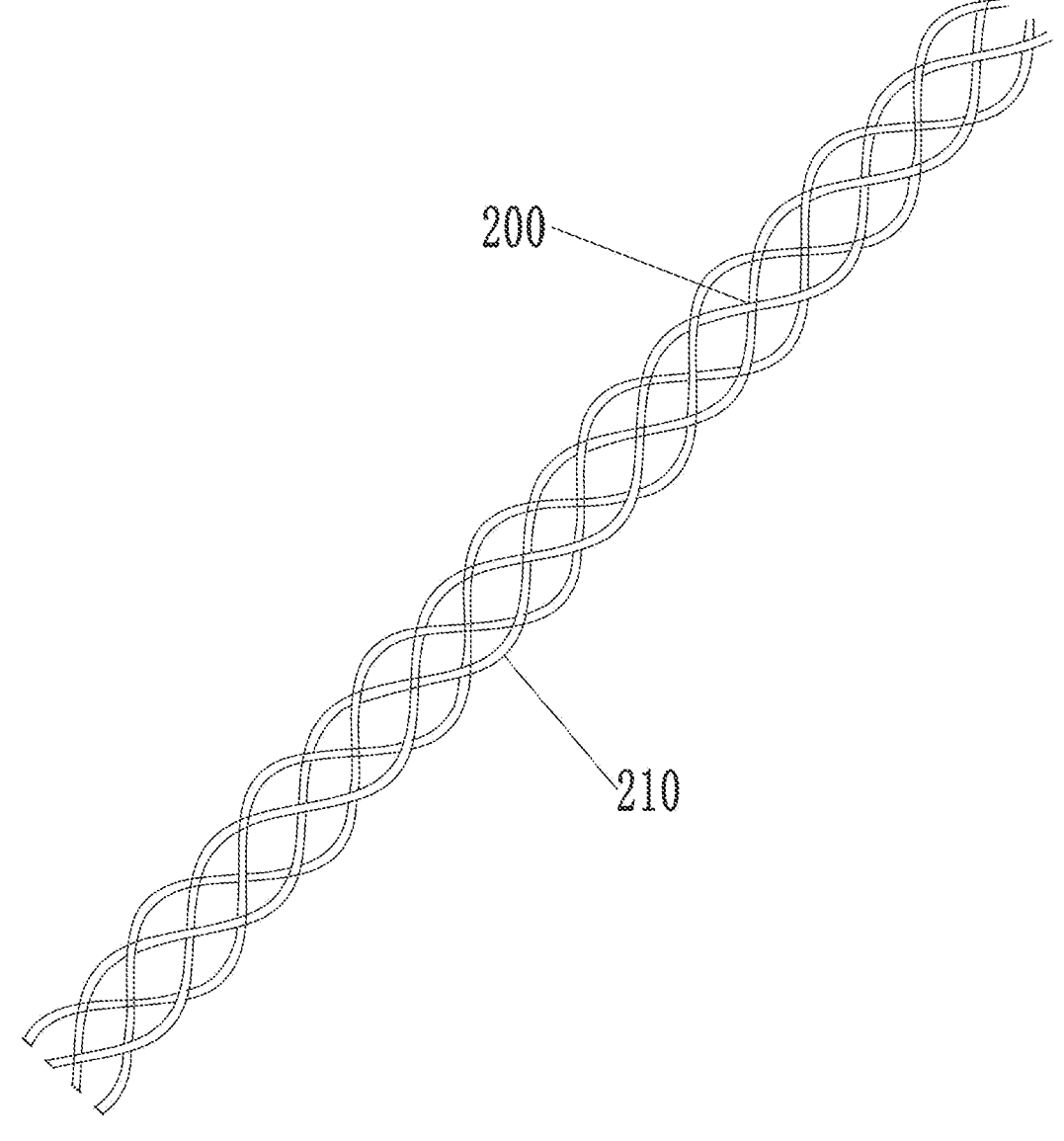
FIG. 7 is a schematic view of a first inner structure according to an embodiment of the disclosure.

Referring to FIG. 7, the inner structure 200 is formed by preparing four strands of the second wire 210 interlaced with one another.

Figure 8:
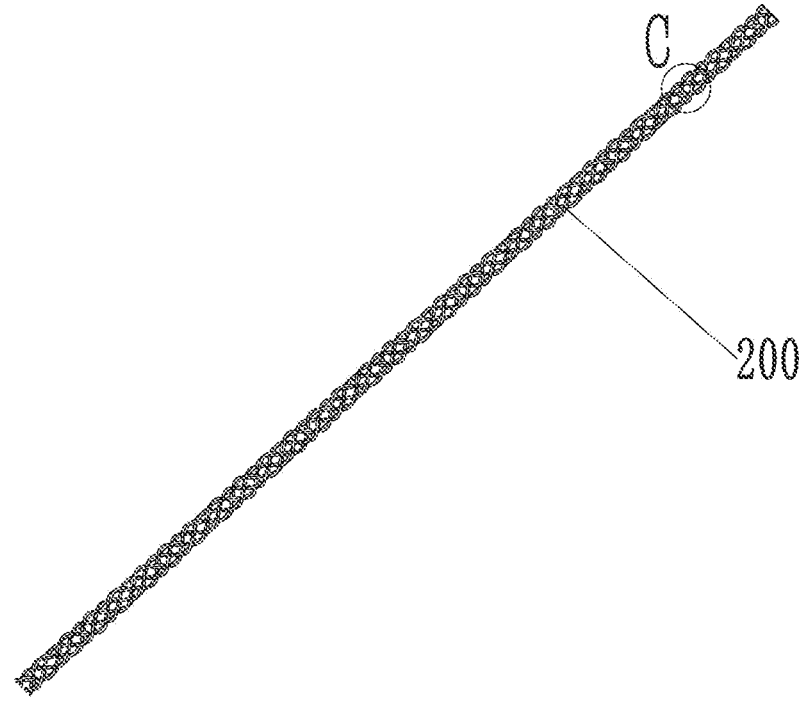
FIG. 8 is a schematic view of a second inner structure according to an embodiment of the disclosure.
Figure 9:
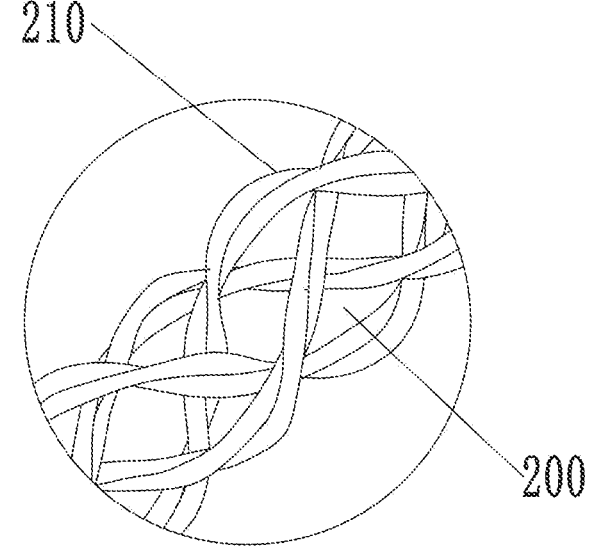
FIG. 9 is an enlarged view illustrating the area C of FIG. 8.

Referring to FIGS. 8 and 9, the inner structure 200 is formed by preparing four groups of wire strands interlaced with one another, and each one group of wire strands is formed by two threads of the second wire 210 intertwining with each other.

Apparently, it is conceivable that the inner structure 200 may be formed by four strands of the second wire 210 intertwined in a clockwise direction.

Figure 10:
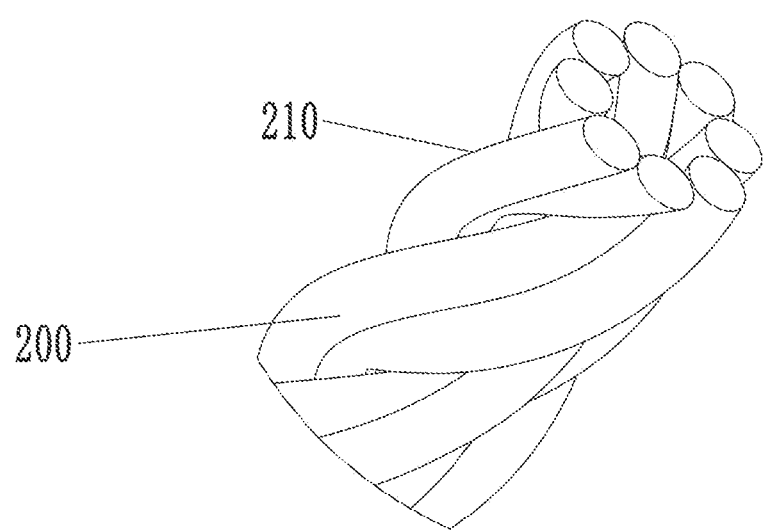
FIG. 10 is a schematic view of a third inner structure according to an embodiment of the disclosure.

Referring to FIG. 10, the inner structure 200 is formed by four groups of wire strands intertwined in a clockwise direction, and each one group of wire strands is formed by two threads of the second wire 210 intertwining with each other.

Figure 11:
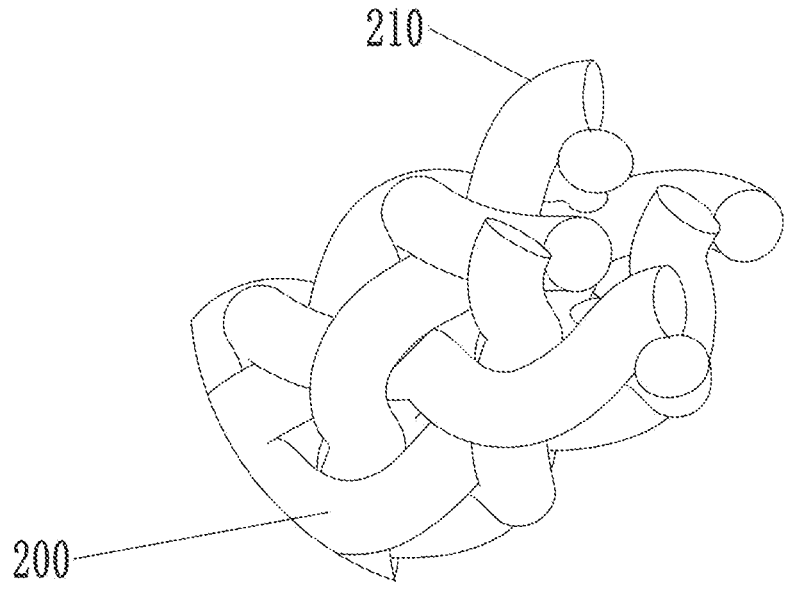
FIG. 11 is a schematic view of a fourth inner structure according to an embodiment of the disclosure.

Referring to FIG. 11, the inner structure 200 is formed by eight threads of the second wire 210 intertwining in a first direction, and adjacent two threads of the second wire 210 intertwine in a second direction opposite to the first direction.

In order to improve support function of the ureteral stent, the inner wall of the outer structure 100 can tightly abut against the outer wall of the inner structure 200. In such a case, the inner structure 200 can support the outer structure 100 well. In the case that both inner and outer layers are made from wires, the urine not only can flow in the outer wall gap of the outer structure 100 and the inner wall gap of the inner structure 200, but also can permeate through the gaps between the interlaced wires of the inner and outer layers.

It should be noted that the ureteral stent according to all aspects of the disclosure may be combined in a single application of the ureteral stent with excellent functions.

The description of embodiments of the invention described above in detail in conjunction with the drawings is not intended to limit the scope of the invention in any form. The invention is intended to cover all changes made by those skilled in the art without departing from the concept of the invention.

The invention claimed is:

1. A ureteral stent, comprising:
an inner structure, and
an outer structure sleeved on the inner structure,
wherein the outer structure is a tube-shaped structure that is knitted with a first wire and is radially compressible; the inner structure is a rope-shaped structure that is woven with a second wire and is radially uncompressible, and both the first wire and the second wire provide fluid guiding gaps that guide fluid.

2. The ureteral stent according to claim 1, wherein the first wire is an elastic thread.

3. The ureteral stent according to claim 2, wherein the first wire is a memory alloy thread.

4. The ureteral stent according to claim 1, wherein the first wire is bent to form loops passing through one another to constitute the outer structure.

5. The ureteral stent according to claim 1, wherein segments of the first wire interlacing in a first direction and a second direction constitute the outer structure, wherein the first direction and the second direction are perpendicular to each other.

6. The ureteral stent according to claim 1, wherein both ends of the ureteral stent are bent, and the two ends of the ureteral stent are bent in opposite directions.

7. A manufacturing method of a ureteral stent, for manufacturing the ureteral stent according to claim 1, comprising steps of:
knitting the outer structure with the first wire,
weaving the inner structure with the second wire, and
then sleeving the outer structure on the inner structure.

8. The manufacturing method of a ureteral stent according to claim 7, comprising: using a knitting method, in which the first wire is bent to form loops passing through one another to constitute the outer structure.

9. The manufacturing method of a ureteral stent according to claim 7, comprising: using a weaving method, in which segments of the first wire interlace with one another in a first direction and a second direction to constitute the outer structure, wherein the first direction and the second direction are perpendicular to each other.

* * * * *